United States Patent [19]

van Eijk

[11] Patent Number: Plant 7,223

[45] Date of Patent: Apr. 24, 1990

[54] IRIS PLANT NAMED PARIS

[75] Inventor: Joseph P. van Eijk, Ve Bennekom, Netherlands

[73] Assignees: H. J. A. Rooyakkers B.V.; World Flower B.V., both of Netherlands

[21] Appl. No.: 336,020

[22] Filed: Apr. 10, 1989

[51] Int. Cl.[5] ..... A01H 5/00

[52] U.S. Cl. ..... Plt./68

[58] Field of Search ..... Plt./68, 87.2

*Primary Examiner*—Howard J. Locker

*Attorney, Agent, or Firm*—Foley & Lardner, Schwartz, Jeffery, Schwaab, Mack, Blumenthal & Evans

[57] ABSTRACT

An iris plant named Paris having large flowers, with both the inner and outer petals being medium to dark violet blue and the limbs of the outer petals containing a generally central yellow band extending from the base approximately one-third the length of the limb. The new cultivar has excellent flower keeping qualities and responds well to forced flowering.

1 Drawing Sheet

The present invention comprises a new and distinct cultivar of iris plant, botanically known as *Iris tingitana,* and commonly known as Dutch iris. The new cultivar is named Paris.

The new cultivar was originated from a cross made by applicant in a controlled breeding program in Wageningen, The Netherlands. The female, or seed, parent was a light blue *Iris tingitana* cultivar not identified by varietal designation or breeding number. The male, or pollen, parent was also an unnamed *Iris tingitana* cultivar, dark blue in color.

Paris was discovered and selected by applicant as a flowering plant within the progeny of the stated cross in a controlled environment in Wageningen, The Netherlands. Asexual reproduction of the new cultivar by division of roots, as performed by applicant at the Institute for Horticultural Plant Breeding, Wageningen, The Netherlands, has demonstrated that the combination of characteristics as herein disclosed for the new cultivar are firmly fixed and retained through successive generations of asexual reproduction.

Paris has not been observed under all possible environmental conditions. The phenotype may vary significantly with variations in environment such as temperature, light intensity and day length. The following observations, measurements and values describe the new cultivar as grown in Wageningen, The Netherlands under conditions which closely approximate those generally used in commercial practice.

The following traits have been repeatedly observed and are determined to be basis characteristics of Paris which in combination distinguish this iris as a new and distinct cultivar:

1. Large flowers having purple-blue flower color.
2. The plant is 95 cm–100 cm in height.
3. The bulbs are longer and less round than the normal shaped iris bulb.
4. Excellent response to forced flower production.
5. Excellent flower keeping qualities.

The new cultivar is similar in flower color to the *Iris hollandica* cultivar Telstar, but Paris has greater height, longer and less round bulbs, and a better response to forced flower production.

The accompanying photographic drawing shows a single flower and foliage of a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions at approximately 12 noon in Breezand, The Netherlands.

Botanical classification: *Iris tingitana* c.v. Paris.

Parentage:

*Male parent.*—An unnamed *Iris tingitana* cultivar (light blue).

*Female parent.*—An unnamed *Iris tingitana* cultivar (dark blue).

Propagation: The new cultivar holds its distinguishing characteristics through successive propagations by division of rhizomes.

Plant:

*Growth.*—Average height and average sturdiness.

*Form.*—One main stem with one or two flowers.

*Stems.*—1, 95–100 cm in length and straight; green in color.

*Foliage.*—50–100 cm in length, upright and erect, tip acute; typical green in color.

Flowers:

*Buds.*—Size: 11 cm in length. Opening: Normal, emerging from foliage sheath. Color: Green. Spathe: Normal.

*Bloom.*—Size of entire bloom: 12–13 cm in diameter. Shape and color of outer petals: Outermost petals or falls generally oblong with the claw somewhat tapering; upper surface approximately 90D with darker veins and a purple border; central stripe or variegation approximately 17C having noticeable borders of 156A-B; the limb is round and convex and curved downwardly perpendicular to the claw, with the edge being somewhat wavy and crenate; the limb color is approximately 90A with darker veins, with a central band or strip of 17A extending to approximately ⅓ of the length of the limb, with the band having an irregular, light border; the underside color of the claw is approximately 83B, with the central band or stripe being 154A, the limb being approximately 90A, with the limb band somewhat widening and approximately 7B. Shape and

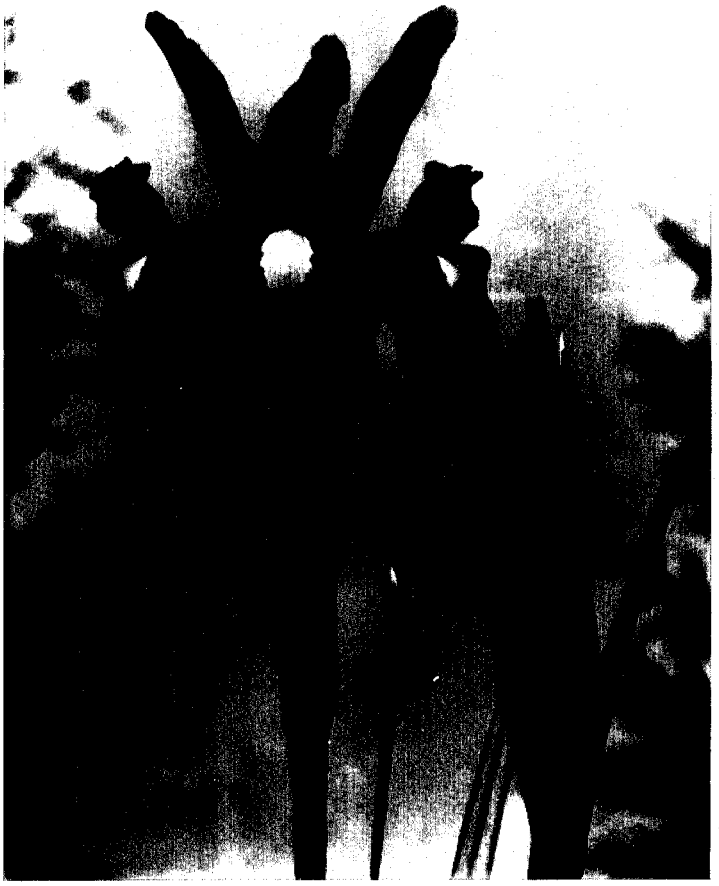

Color of Inner Petals: The limbs are narrow, elliptic, concave, with the edge wavy and very slightly crenate; color somewhat more purple than 93B; a very narrow yellow stripe extends from the base approximately ¼ of the length of the band; the outside surface of the inner petals are similar to the inside although no yellow stripe appears. Keeping qualities: Excellent compared to similar cultivars of this type. Blooming habit: Excellent; very responsive to forced flowering. Fragrance: Barely scented. Beard: Border somewhat wrinkled and irregularly crenate; upper and under surface approximately 90A.

Reproductive organs: The stamens with filaments approximately as long as anther and base, and white with a hint of purple; anther light yellow, pollen yellow; pistil leaf-shaped, bridge curved outward, convex, oblong and widening; dark purple ridge, with the border being generally purple 86A having an outer band 78A blending into a thin somewhat translucent border edge.

I claim:

1. A new and distinct cultivar of iris plant named Paris, as illustrated and described.

* * * * *